(12) United States Patent
Flesch (10) Patent No.: US 7,081,093 B2
(45) Date of Patent: Jul. 25, 2006

(54) ARRAY TRANSDUCER FOR 3D TILTING PROBES

(75) Inventor: Aimé Flesch, Andrésy (FR)

(73) Assignee: Vermon, Tours (FR)

( * ) Notice: Subject to any disclaimer, the term of this patent is extended or adjusted under 35 U.S.C. 154(b) by 0 days.

(21) Appl. No.: 10/727,589

(22) Filed: Dec. 5, 2003

(65) Prior Publication Data

US 2005/0124889 A1    Jun. 9, 2005

(51) Int. Cl.
*A61B 8/14* (2006.01)
(52) U.S. Cl. .................................... 600/459
(58) Field of Classification Search ........ 600/437–472; 310/330–334; 128/916; 73/625, 626; 367/7, 367/11, 130, 138
See application file for complete search history.

(56) References Cited

U.S. PATENT DOCUMENTS

| | | | |
|---|---|---|---|
| 5,070,879 A * | 12/1991 | Herres | 600/444 |
| 5,152,294 A | 10/1992 | Mochizuki et al. | |
| 5,159,931 A | 11/1992 | Pini | |
| 5,460,179 A * | 10/1995 | Okunuki et al. | 600/444 |
| 6,213,948 B1 | 4/2001 | Barthe et al. | |
| 6,572,548 B1 * | 6/2003 | Cerofolini | 600/443 |
| 2003/0055338 A1 | 3/2003 | Steininger et al. | |

* cited by examiner

*Primary Examiner*—Ali Imam
(74) *Attorney, Agent, or Firm*—Ross F. Hunt, Jr.; Stites & Harbison, PLLC (57) ABSTRACT

An ultrasonic apparatus is provided for producing three dimensional images using at least one moving curved array transducer for scanning a volume of a region of interest to be imaged. The apparatus includes an acoustic front shell having complex shape and an ultrasonic transducer adapted for swinging movement underneath the front shell and having a front surface of a shape conforming to the complex shape of the front shell. A motor provides the swinging movement of the ultrasonic array transducer underneath the front shell so as to scan a volume of the region of interest. The shell and a transducer carrier may be of an ovoid shape. The transducer may include lips at superior edges thereof which contain a coupling grease. Multiple transducers for different applications may be employed.

22 Claims, 4 Drawing Sheets

ARRAY TRANSDUCER FOR 3D TILTING PROBES

FIELD OF THE INVENTION

This invention relates to the construction and manufacturing of an ultrasonic 3D probe which incorporates an array transducer for mechanically scanning an angular sector. The mechanical movement of the transducer is preferably obtained by tilting or swinging the transducer around its azimuthal longitudinal axis, and such probes are typically dedicated to use in medical diagnosis or in the non-destructive evaluation of materials.

BACKGROUND AND RELATED ART

The use of volumetric image rendering techniques in ultrasonic scanning is becoming one of the most exciting modalities in modern medical diagnostics. Currently, a number of sophisticated systems are capable of 3D imaging and surface representation that provide patients and users with both figurative images and comprehensive data information. The diagnostic results can be displayed either as surface images (3D) or as 2D scanning representations (i.e., a conventional representation) in order to give better detail.

Among the most important advantages of 3D systems is the capability provided thereby of scanning a volume of the organ for imaging purposes and then storing the entire information obtained in a manner so as to be able to display the desired scanning plane by simply positioning a cursor on the surface of the related organ. This capability allows the diagnosis to be reduced to a single-pass scanning action in obtaining all of the useful information.

To provide imaging system with 3D scanning capability, several probe technologies have been developed and are commercially available today. Generally speaking, ultrasonic scanning probes having a 3D capability currently belong to three construction sub-groups: matrix arrays or fully electronic probes (wherein all scanning is done by electronic phasing), moving phased arrays or hybrid probes (wherein one scanning operation is carried out by electronic phasing while a second is performed mechanically using a motor drive) and 2D mechanically moving transducers or fully mechanical probes (wherein mechanical scanning in both directions is provided).

The matrix array approach uses arrayed transducers having vibrating elements disposed in two crossing directions so as to form an emission surface. The vibrating element sizing of these transducers should be on the order of the transducer wavelength, and thus this approach requires a very large number of vibrators (typically more than 3000) that must be addressed.

Moving phased arrays are more commonly used because of their relative simplicity of construction and the possibility of using existing imaging systems (for software updating and motor control).

Finally, 2D mechanical moving transducer devices are much less commonly commercially available because of the intricate moving mechanism employed and the associated effective lack of reliability.

Presently, most 3D ultrasound imaging systems or 3D upgradeable systems are equipped with hybrid probes wherein an electronic array transducer is swung, tilted or rotated to enable impinging of a volume sonification. Transducers such as phased-arrays, linear arrays (straight and curved) and 1.5D arrays are suitable for this purpose. Commonly, the transducer is mounted in a coupling liquid bath which is formed by the probe housing. A motor is then coupled to the transducer carrier and the front shell of probe is made up of acoustically transparent material so as to not disturb sound propagation path. However, solid state materials that perfectly match the acoustic impedance of the human body and the coupling liquid do not exist in practice so that artifacts are usually encountered on the resultant images and these contribute to degrade the quality of system. Different potential solutions and technical approaches have been attempted to improve the coupling problem between the array transducer and the probe shell and these efforts have been more or less successful. However, the general problem is even more complicated with systems employing curved linear array transducers.

Considering some examples of the related prior art, U.S. Pat. No. 5,159,931 to Pini discloses an ultrasonic apparatus which enables three dimensional reconstruction of anatomical structures. According to this patent, the volume is obtained either by rotating a sector scan transducer of an angle of 180 degrees or by using a matrix array. The patent relates generally to an apparatus including a phased array transducer which is rotated by means provided for this purpose. Thus, a principle is stated with some limitations, but no detail is provided on how the transducer is acoustically coupled to the probe shell.

In U.S. Published Patent Application No. 2003/0055338 to Steininger et al, an ultrasonic probe for endosonography is disclosed which includes a transducer array pivotally mounted on the probe housing and coupled to means for providing rotation thereof around an axis of rotation. The transducer array is constructed in such a manner as to be able to swing through a sector of angle underneath the probe front shell. This method allows the probe to scan regions of an organ that are normally not seen by probes having a fixed transducer. A stepper motor is coupled to the transducer to provide the apparatus with accurate positioning and movement. A coupling fluid is used to fill the space separating the transducer as well as the interior surface of the probe shell. Unfortunately, in practice, the coupling fluid volume located between the transducer and the probe front shell is responsible for acoustic artifacts which are visible in the proximal zone of the resultant images.

The basic concept disclosed in the Steininger et al patent is similar to that disclosed in U.S. Pat. No. 5,152,294 to Mochizuki et al wherein a three dimensional ultrasonic scanner of hybrid type is described. An array transducer of a curved shape is provided internally. A coupling fluid bath is disposed between the transducer and the probe front shell. A volume of liquid is limited by a flexible membrane sealed to the edges of the transducer and the periphery of the front shell. This construction prevents the drive means (motor) from being exposed to liquid immersion. In a manner designed to reduce acoustic artifacts from being formed through the coupling bath as described above, the longitudinal radius of curvature of the transducer is made smaller than that of the corresponding internal surface of probe front shell so as to provide oblique reflection of acoustic energy emitted from, and received by, the transducer. Further, an absorbing material is disposed at the extremities of the front shell to cancel ultrasonic waves hitting this area, so no return echoes are produced. However, this method of reflecting echo suppression results in a complicated probe construction and the acoustic path for every single element of array is inherently modified, from the center to the outermost elements of the array, thereby creating an undesired apodisation function. Another shortcoming of this approach concerns the liquid bath surrounding the transducer; strong liquid turbulences will occur when the movement of the transducer is accelerated, thereby resulting in increased resistance to transducer movement and in consequent higher energy consumption by the drive means.

U.S. Pat. No. 6,213,948 to Barthe et al describes a three dimensional ultrasound imaging probe wherein an array transducer swings over a concentric radius with the probe front shell so as to continuously maintain the same distance between all of the transducer elements and the shell. The volume of coupling fluid is also controlled so as to be a minimum, to thereby ensure that the size of the probe is compatible with clinical use.

Although the Barthe et al patent discloses an interesting approach to maintaining the liquid bath at a constant distance with respect to the probe shell over the entire surface of transducer, this approach is only suitable for flat linear or flat phased arrays wherein the transducer can be manufactured with an elevational front curvature equal to that of the probe front shell. As disclosed in the Barthe et al patent, the transducer elevational section is at a constant spacing from the shell, thereby optimizing the acoustic path thereof. Unfortunately, an extension of this approach to probes using curved linear array transducers which are based on swinging or tilting of the transducer is inhibited or prevented by the fact that while the array transducer still exhibits same elevational radius of curvature over the azimuth length thereof, the internal surface of the probe shell will have the radius of curvature thereof changed from the center (the largest change) to the edges (the smallest) as the intersection of two curved surfaces, one along the azimuth and the other along the elevation. In fact, for curved array based hybrid probes, the more the transducer azimuth axis is curved, the higher the difference in the radius of curvature of the shell. Therefore, in some regions of the transducer front face, the lens surface, or the external surface of transducer will not be parallel to the internal surface of shell. As a consequence, the transmitted ultrasonic waves are inherently bent at a deviation angle according to the difference in refraction index between the lens material and the coupling liquid. This phenomenon is even more marked with temperature change, where the refraction index of the liquid will vary much more than that of the corresponding solid materials such as those of the lens or probe shell. Generally speaking, if no aberration correction is provided by the imaging system, as is usually the case, a degradation of the image quality can be observed at the sides of images.

In view of all of the above shortcomings and drawbacks of prior art three dimensional probes and, more particularly, of curved linear array transducer-based swinging probes (hybrid devices), there is obviously a need for improved three dimensional hybrid probe constructions wherein acoustic artifacts, due to the coupling fluid, are avoided and higher tilting rates and acceleration of the transducer in the probe housing are permitted.

SUMMARY OF THE INVENTION

According to the invention, there is provided an improved swinging or pivoting curved array transducer-based scanning device, i.e., a so-called hybrid probe, for producing three dimensional imaging. The invention is preferably embodied as a scanning probe having smooth shapes and forms so as to facilitate the handling of the probe device by users. A coaxial cable bundle provides signal transmission between elementary transducers and an imaging system interface, and a connector provided at the termination of the cable bundle.

It is noted that the terms "pivoting" or "pivoting axis" are used in describing a transducer device having a rotational axis around which the device is said to be swinging or tilting. The terms "swinging" and "tilting" refer to alternative rotation of the device which describes a predetermined sector angle. The term hybrid probe designates an ultrasonic probe for producing three dimensional images which is provided with a mechanically swinging or tilting array transducer. The term shell is used to designate the front protective cover of the imaging probe at which is located the acoustic window of the probe.

In one preferred embodiment of the invention, a 3D ultrasonic probe using a swinging curved array transducer is provided wherein the probe preferably includes a curved array transducer having a front surface of a convex shape such as enables sector scanning of an organ to be carried out. Of course, a flat-shaped linear array transducer can be provided instead, with no change in the applicable principle.

The preferred transducer configuration, i.e., a curved array configuration, is of widespread use in gynecology/obstetrics, abdomen, cardiac and endosonography examinations. In general, the radius of curvature (RoC) of the curved array configuration is defined with respect to the morphology of the organs to be imaged and the depth of the image. Typically, the curved array scanning probes are provided with a radius of curvature (RoC) which ranges from 10 mm (endosonography) to 150 mm (examinations of the abdomen) so as to cover a whole range of applications but the RoC can be extended as desired without limitation. In order to optimize the lateral resolution of the acoustic output, the array transducers are either equipped with a focusing lens at the front surface of the probe, or are hard focused in elevation. Because a curved line provides scanning of a sector shaped portion by pivoting thereof around a longitudinal axis, a convex surface results which is determined by the intersection of a first RoC (that of the transducer) and a perpendicularly oriented second RoC (that defined by the transducer movement).

In accordance with one aspect of the invention, in order to improve the contact between the probe front shell and the surface of the transducer, the transducer focusing lens or the external transducer surface is shaped so as to perfectly fit with and conform to the internal surface of the shell, so there is no focal aberration created that must be corrected. Further, because the RoC in elevation of the shell shifts or varies from the center to the edges of the shell, the RoC of the transducer lens is made to shift or vary accordingly. In an important implementation, to achieve such a variation in the RoC of transducer lens, the piezoelectric member of the array transducer has a progressively curved shape in elevation. This also compensates for other above-mentioned effects. It is noted that this progressively curved shape of the piezoelectric member can be obtained by using composite substrates wherein the flexibility of the material used facilitates the shaping of the device. Other types of materials are, of course, available and can be used but require more complicated machining processes to achieve the desired shaping as well as require increased care in the handling and manipulation thereof.

In accordance with a further aspect of the invention, there is provided an ultrasonic apparatus for producing three dimensional images using at least one moving curved array transducer for scanning a volume of a region of interest to be imaged, the apparatus comprising:

an acoustic front shell having complex shape;

an ultrasonic transducer adapted for swinging movement underneath said front shell and having a front surface of a shape conforming to the complex shape of said front shell; and drive means for providing said swinging movement of the ultrasonic array transducer underneath said front shell so as to scan a volume of the region of interest.

Preferably, in an embodiment wherein the apparatus comprises a mechanical probe, the drive means comprises a motor mounted in direct driving relation with the transducer through the rotation axle of the transducer.

In another embodiment wherein the apparatus comprises a mechanical probe, the array transducer is of a curved linear shape, and the front shell has an internal surface, all of the front surface of the transducer conforms to the complex shape of the internal surface of the front shell.

According to a further aspect of the invention, there is provided an ultrasonic curved array transducer for use in a three dimensional mechanical imaging probe, including a front shell, having an internal surface, disposed in front of the transducer, the transducer comprising:

an external focusing lens made of silicon rubber and including a front face having variable radius of curvature exactly corresponding to that of the front shell in front of said transducer, said variable radius of curvature varying in a manner such as to minimize the distance separating the front face of the focusing lens and the internal surface of the shell, and a piezoelectric member for emitting and receiving ultrasonic energy, said piezoelectric member being assembled beneath said focusing lens and having a variable surface curvature compensating for the variable radius of curvature of the focusing lens in a manner such as to enable the transducer to maintain a common elevational focus for all transducer elements of the array transducer, said transducer having an external elevation surface profile parallel to the corresponding internal profile of the front shell of the probe.

In one preferred embodiment, the piezoelectric member has a radius of curvature which varies from a concave shape at a center region of the array transducer to a flat shape at outer regions of the array transducer.

In another preferred embodiment, the piezoelectric member has a radius of curvature which varies from a concave shape at a center region of the array transducer to a convex shape at outer regions of the array transducer.

In yet another preferred embodiment, the piezoelectric member has a radius of curvature which varies from a flat shape at a center region of the array transducer to a convex shape at outer regions of the array transducer.

In a further preferred embodiment, the piezoelectric member has a radius of curvature which varies from a concave shape at a center region of the array transducer to a flat shape at an intermediate region of the array transducer and to a convex shape at outer regions of the array transducer.

The piezoelectric member is preferably made from a composite ceramic/polymer structure.

In accordance with yet another aspect of the invention, there is provided an ultrasonic mechanical probe comprising a moving array transducer, the moving array transducer comprising lips disposed at superior edges of the moving array transducer for retaining a quantity of a coupling grease.

In one preferred embodiment, the lips are made of silicon rubber.

In another preferred embodiment, the lips are made of elastomeric rubber.

According to a further aspect of the invention, there is provided an ultrasonic apparatus for producing three dimensional images using a swinging or tilting ultrasonic array transducer, the further apparatus further comprising:

a probe housing having an ovoid portion in which the array transducer is mounted and having an internal surface and a central axis;

an ovoid shaped carrier of a shape conforming to the internal surface of the said probe housing, said array transducer comprising at least one curved array transducer having a longitudinal axis and being mounted at an angular position within said carrier so as to directly couple acoustic energy to the probe housing and hence to an external media; and motorization means disposed at the central axis of the ovoid carrier for tilting or swinging the transducer around said longitudinal axis.

The curved array transducer of the ovoid carrier preferably has an external surface conforming to the corresponding internal surface of the probe housing.

Preferably, the ovoid carrier is shaped such that any space between the external surface of said ovoid carrier and the internal surface of the probe housing is reduced to a minimum and the space is filled by a thin film of coupling liquid or grease.

The motorization means preferably comprises rotational motorization means located at a center portion of the ovoid carrier so as to provide rotation of the ovoid carrier around a central axis.

The ovoid carrier preferably includes a central hollow space in which is located interconnection means for transducer elements of said array transducer.

In an important implementation, the ovoid carrier comprises at least a first curved array transducer mounted at a first angular position and a second curved array transducer mounted at a second angular position so as to enable the probe to simultaneously scan two distinct informational volumes.

In a further important implementation, the ovoid carrier comprises at least one first curved array transducer mounted at a first angular position and dedicated to imaging applications and a second curved array transducer mounted at a second angular position and dedicated to high intensity operations in therapy applications. Preferably, the imaging operation for a given region of interest can be replaced by a high intensity operation using said second transducer operating in the given region.

In one preferred embodiment, the ovoid carrier is capable of rotating through an angle of more than 360 degrees without damage to interconnection means for said array transducer.

In another preferred embodiment, the ovoid carrier is provided with at least two oppositely curved array transducers and the ovoid carrier is capable of rotating through an angle up to 180 degrees.

A very important object of the present invention is to provide a method and apparatus for producing three dimensional images which employs the hybrid type of scanning probes for scanning a volume of the region of interest.

It is another object of the invention to provide a method and apparatus for producing 3D images that uses a curved linear array transducer pivoted or rotated around an axis to form the desired scanning angle in the elevational plane of the transducer.

It is still another object of the invention to provide a method and apparatus for producing 3D images that include a curved linear array transducer which is adapted to be pivoted or rotated around an axis and which, in use, is in physical contact with the probe shell over the surface of transducer.

It is yet another object of the invention to provide a method and apparatus for producing 3D images that includes a curved linear array transducer adapted to be pivoted or rotated around an axis, the transducer having a thin film of coupling grease provided at the interface between the transducer surface and the probe shell, and including a lens having an external face of a shape matching or conformal to the internal surface of the probe shell.

It is still another object of the invention to provide a method and apparatus for producing 3D images that includes a curved array transducer adapted to be pivoted or rotated around an axis and of shape conformal to the internal surface of the probe shell, the transducer further including a piezoelectric member having a surface of progressive curvature in elevation such as to compensate for the focalization variation effect of the lens when shifting from the center to the edges of the array transducer.

It is another object of the invention to provide a method and apparatus for producing 3D images that uses an ellipsoid or ovoid shaped transducer and a transducer carrier pivoted around the longitudinal axis thereof, the transducer including a lens having an external surface conformal to the internal surface of the probe shell such as to avoid liquid bath effects present in prior art devices.

It is yet another object of the invention to provide a method and apparatus for producing 3D images that uses an ellipsoid or ovoid shaped transducer and a transducer carrier pivoted around an axis and having electric interconnection means provided along the longitudinal axis of the ellipsoid or ovoid in a manner such as to allow the transducer to swing through with an angle more than 360 degrees.

Further features and advantages of the present invention will be set forth in, or apparent from, the detailed description of preferred embodiments thereof which follows.

DESCRIPTION OF THE PREFERRED EMBODIMENTS

Figure 1:
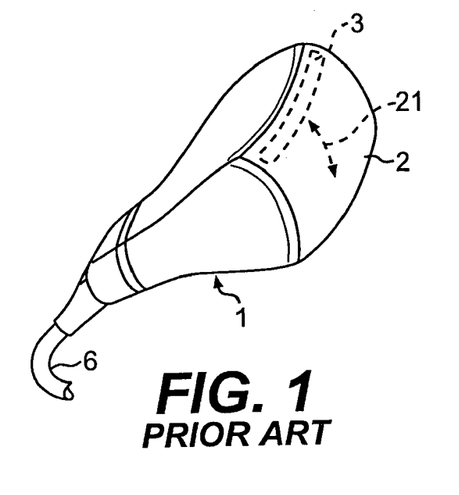
FIG. 1 is a perspective view of a typical prior art hybrid ultrasonic probe for three dimensional applications including a swinging array transducer.

As illustrated by the prior art discussed above, three dimensional hybrid probes for medical diagnostic use have been developed and described. However, all prior art devices are affected with similar shortcomings that limit their widespread commercial use. FIG. 1 illustrates an ultrasonic hybrid probe 1 equipped with a swinging/tilting curved array transducer 3 disposed underneath the front shell 2 of the probe 1. The transducer 3 is conventionally caused to rotate or swing in a coupling liquid bath so that acoustic energy is emitted from, and received through, the front shell 2. Transducer 3 conventionally comprises a plurality of elementary vibrators uniformly disposed along the azimuth axis thereof to provide electronic scanning of images. Probe 1 also comprises an internal mechanism (not shown) that carries transducer 3, and a motorization means (not shown), i.e., an electric motor drive, for providing swinging of the transducer. The transducer 3 is secured to the internal mechanism and movement thereof is produced by the motor. The movement of transducer 3 is indicated in FIG. 1 by arrow 21. A coaxial bundle of cables 6 is provided as an interconnection means between transducer 3 and the corresponding imaging system (not shown).

Figure 3:
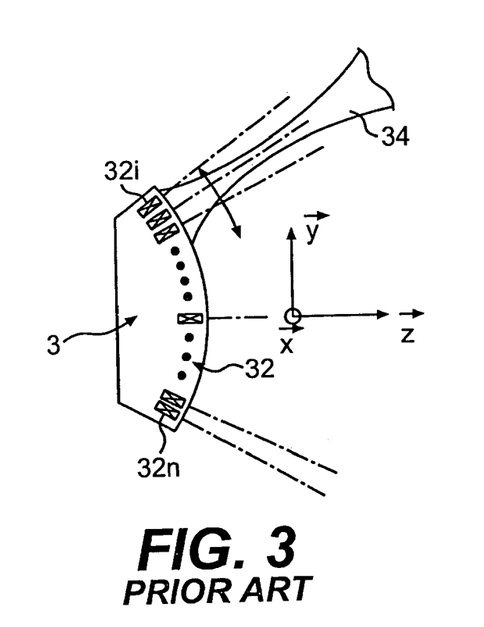
FIG. 3 is a schematic cross sectional view of a prior art curved linear array transducer.

Further details of transducer 3 can be seen in FIG. 3 where the transducer 3 is illustrated in azimuthal sectional view. As illustrated, vibrators 32 (32$i$ . . . 32$n$) of transducer 3 are disposed in an arcuate arrangement along the front surface of transducer 3. All vibrators 32 are of an identical design and preferably operate at a same frequency as well. Normally, as described below in connection with FIG. 4, each vibrator 32 is built from a portion of a piezoelectric member (not shown) which is then sandwiched between a backing material (not shown in FIG. 3) disposed at the rear side thereof and one or more acoustic matching layers (not shown) laminated on the front face thereof. The piezoelectric material can advantageously be made of polycrystalline ceramics or ceramic/polymer composites or single crystals, etc.

During operation, the members of a group of vibrators 32 are addressed together by the system, using a predetermined time delay for each, so as to form a focused acoustic beam indicated at 34. The acoustic beam 34 can also be produced with a continuous focal shifting capability and, optionally, with an electronic steering capability. To achieve complete scanning over the transducer surface, the acoustic beam 34 is then moved along the surface of the transducer 3 in the directions indicated by the double headed arrows 33, and the scanning rate is governed by the penetration depth and the number of lines to be performed for each scan. This type of scanning is commonly called "electronic sector scanning."

Figure 2:
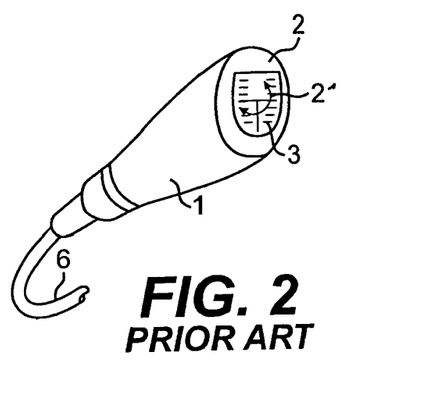
FIG. 2 is a perspective view of another typical prior art hybrid ultrasonic probe for three dimensional applications, including a rotating array transducer.

Another common type of three dimensional hybrid ultrasonic probe using a moving array transducer is shown in FIG. 2. Here, the probe 1 is equipped with a phased array transducer 3 which is mounted underneath the front shell 2 of the probe 1. Shell 2 serves to provide protection for the transducer surface, and the array transducer 3 is rotated around the axis of symmetry thereof as illustrated by the double-headed arrows 21 (alternate rotation). It is important to note that a flat or spherical transducer front face is preferred here in order to maintain good contact with shell 2. Hybrid probes of this type are of quite widespread use because of the simplicity of concept thereof and the ease of their manufacture.

Figure 4:
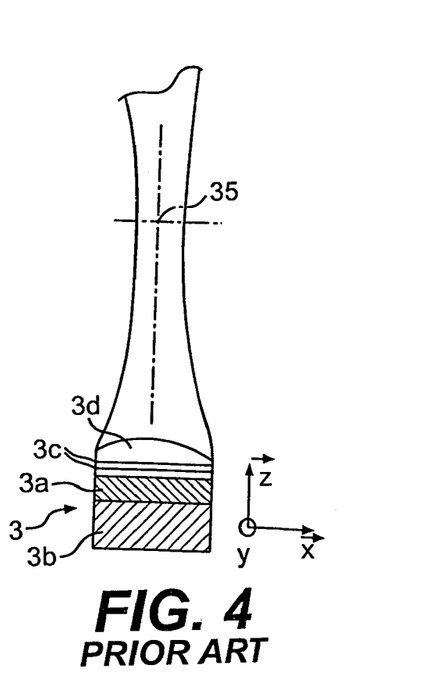
FIG. 4 is a cross sectional view, in elevation, of a prior art transducer.

As indicated above, the details of transducer 3 are better illustrated in the elevation section shown in FIG. 4. Linear array transducers such as those described herein are commonly provided with a rubber elastomer focusing lens 3d attached on the front surface thereof. Lens 3d is conventionally directly molded over the surface of the transducer or, alternatively, bonded onto the surface, with there being no substantial difference in technical result. Because the speed of sound in the lens material (typically silicon rubber) is generally lower than that of the propagation or coupling medium, lens 3d is inherently of a convex shape when a focused acoustic beam is desired.

FIG. 4 also illustrates a cross section of an acoustic beam 36, including a focal point 35, issuing from lens 3d. Of course, in the case where a hard focusing technique (not shown) is used, i.e., where a lens is omitted, the surface of transducer 3 is concave shaped so as to provide the desired focal effect.

FIG. 4 also shows a piezoelectric member 3a, a backing member 3b and a pair of acoustic matching layers 3c, all as described above in connection with FIG. 3.

Figure 5:
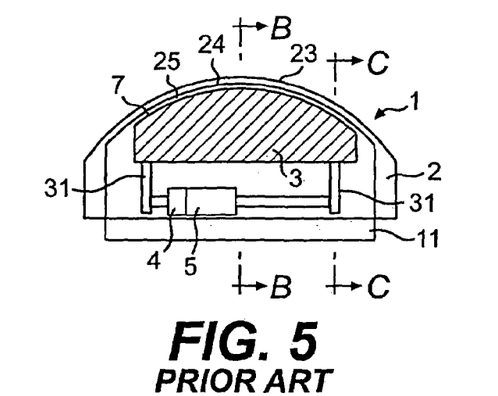
FIG. 5 is a longitudinal cross sectional view of a prior art hybrid probe.

Referring to FIG. 5, in order to provide a better understanding of a main object of the invention, and in order to clearly show the drawbacks of the prior art, probe 1, shown in longitudinal cross section in FIG. 5, is intentionally shown in this cross sectional view in a manner so as to distinguish between the different parts of the probe. As shown, a shell portion of a probe housing 11 is of a convex shape according to the curvature of transducer 3 and its swinging profile, i.e., the profile defined by the transducer 3 during swinging thereof.

Figure 6:
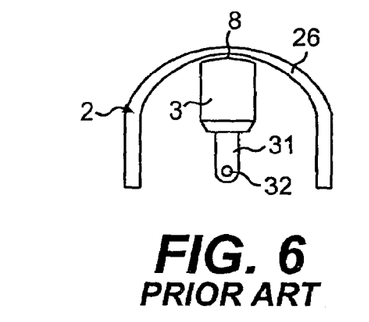
FIG. 6 is a cross sectional view of the hybrid probe of FIG. 5 taken generally along line B—B of FIG. 5.
Figure 7:
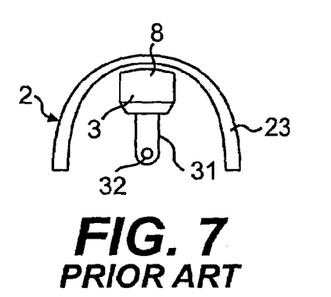
FIG. 7 is a cross sectional view of the hybrid probe of FIG. 5 taken generally along line C—C of FIG. 5.

A motor 4 is secured to a transducer carrier or support 31 and is mounted in alignment with the rotational axis of transducer 3. More particularly, as shown in FIGS. 5, 6 and 7, the transducer 3 is equipped with supports 31 disposed at its two extremities and supported via an axle or shaft 32. Transducer 3 can therefore rotate around the axis defined by axle 32.

Motor 4 is preferably associated with a gearbox 5 so as to be able to provide an acceptable rotational speed and torque in accordance with the specifications of the probe.

Figure 8:
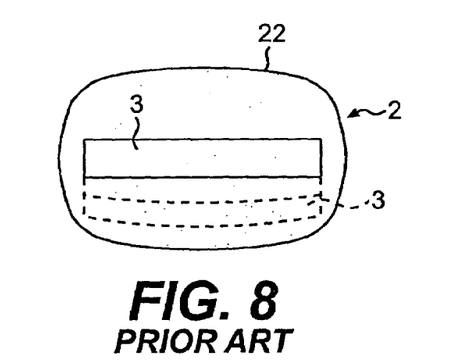
FIG. 8 is a top plan view of a prior art hybrid probe including a swinging array transducer.

The movement of transducer 3 is limited so as to avoid contact with shell 2 as illustrated in FIG. 8. Usually, electronic abutments are provided laterally so as to enable the motor 4 to stop rotation of the transducer 3. In fact, the swinging/tilting movement of transducer 3 is defined or limited by a surface indicated by line or shell 22 of FIG. 8 which corresponds to the hollow space within shell 2.

Further, as shown in FIGS. 6 and 7, this hollow space is covered by a membrane of constant thickness having an external surface 23 and an internal surface 24. This membrane is a so-called "acoustic window." The thickness of the region defined by line 2c is preferably 1 mm or less. Materials such as TPX™, HD Polyethylene, or Polysulfone plastics are good candidates for use in making the membrane. Shell 2 is preferably produced by injection molding or thermoforming or by conventional machining or the like, and any of these various methods can be used with no significant impact on the performance and operating characteristics. Selection of the manufacturing method for shell 2 is generally governed by the desired production quantity and price of the probe. Typically, the "acoustic window" is defined so as to permit swinging of transducer 3 through more than a 30 degree sector without contact with shell 2. A sector angle of 60 degrees is desirable in obstetrics, while a 45 degree section is generally optimal for heart imaging.

FIG. 5 illustrates a conventional prior art hybrid probe wherein the main generating line of transducer 3 is separated from that of shell 2 by a constant space indicated in FIG. 5 at 25. Space 25 is usually filled by a coupling liquid. Receiver shell 2 possesses a complex surface at the region of the acoustic window. FIGS. 6 and 7 show the difference in curvature that can be observed between the elevation RoC of the transducer front face and the RoC of the shell 2, for two separate sections of the probe 1, viz., section B and section C of FIG. 5. In this regard, as illustrated in FIGS. 6 and 7, the internal curvature 24 of the shell 2 and the external curvature 23 of shell 2 are much different depending on the position of observation. However, in the same vein, it will be appreciated that the curvature 8 of the lens of transducer 3 remains the same whatever the position of the transducer 3 so that there is a continuous variation in the geometry of the space 25 separating the transducer 3 and shell 2. Consequently, as mentioned above, the acoustic output of the probe 1 can be significantly affected and its characteristics shifted over the curvature of transducer 3 from the central vibrating element of transducer to the outermost elements.

Figure 9:
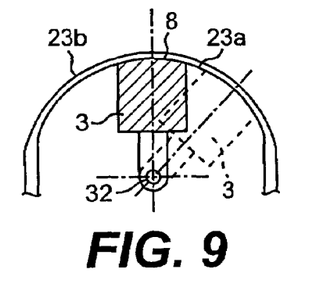
FIG. 9 is a cross sectional view of a hybrid probe in accordance with a preferred embodiment of the invention.
Figure 10:
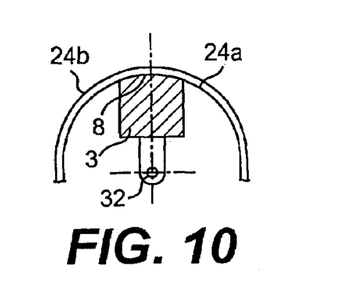
FIG. 10 is another cross sectional view of the hybrid probe of FIG. 9.

Referring to FIGS. 9 and 10, wherein a preferred embodiment of the invention is illustrated, shell 2 and transducer 3 are still provided at two distinct sections of the surface of probe 1. In this embodiment, the transducer 3 is preferably defined as a curved linear shape and the swinging/tilting sector through which transducer 3 rotates or swings is chosen to be smaller than 180 degrees for purposes of simplicity of explanation. As above, transducer 3 is provided with carrier or support and can be rotated around axle 32.

As illustrated, shell 2 possesses an internal surface or internal curvature 24 and an external surface or external curvature 23 that changes progressively from the central area thereof to the edges of the probe. As indicated by FIGS. 9 and 10, the front surface of transducer 3 is shaped in such a manner to provide intimate contact with the surface 24 of the shell. Moreover, this type of contact is provided for the surface of transducer 3 throughout, meaning that the transducer 3 is in surface coupling contact with the shell 2 over its entire front face during rotation of transducer 3. This coupling contact eliminates the need for the use of coupling fluid and thus prevents focal aberrations resulting from such use of a coupling fluid.

As can be observed from FIGS. 9 and 10, the RoC of the transducer lens of transducer 3 must be modified accordingly in order to achieve this end. It is also apparent that the RoC of the transducer lens is smaller in FIG. 10 (which is a cross sectional view taken at the central area of the probe). In fact, the elevation RoCs for the shell 2 and transducer 3 are governed by the azimuth curvature of the transducer 3, and in general, the more the array transducer 3 is curved, the greater the difference in the RoC between the central and the edges areas of the probe. However, while the shell facing surface 9 presented by transducer 3, and formed by the transducer lens, is of a progressively varying shape, it should be understood that making a transducer having variable RoC lens is an undemanding task which does not require any specific skills. Thus, it will be appreciated from the foregoing that a key feature of the present invention concerns the provision of an ultrasonic array transducer with a variable RoC lens which maintains the elevational focus constant over the array.

Figure 11:
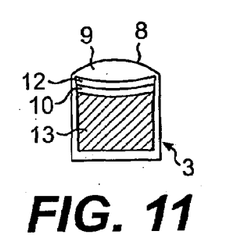
FIG. 11 is a cross sectional view of the array transducer of the hybrid probe of FIGS. 9 and 10.
Figure 12:
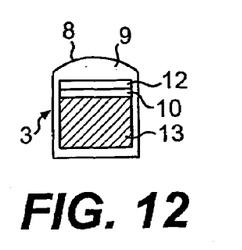
FIG. 12 is a further cross sectional view of the array transducer of the probe of FIGS. 9 and 10.
Figure 13:
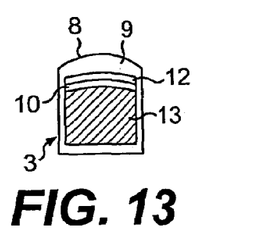
FIG. 13 is yet another cross sectional view of the array transducer of the probe of FIGS. 9 and 10.

In view of the foregoing goal, the RoC of the transducer lens should be modified accordingly, and FIGS. 11, 12 and 13 show three different sections of a transducer wherein the piezoelectric member 10 and matching layer member 12 are accordingly shaped to compensate for the variation in the lens effect. More specifically, the objective of the constructions shown in FIGS. 11, 12 and 13 is to preserve the focal degree of the transducer whatever the RoC of the lens. In an extreme configuration, the variation of the RoC provided for the silicon transducer lens is so important that the required shape compensation carried out with respect to the piezoelectric member 10 starts from the concave shape illustrated in FIG. 11, progresses to the flat shape shown in FIG. 12 and finally ends with a convex shape as illustrated in FIG. 13.

Considering FIGS. 11, 12 and 13 in more detail, FIG. 11 shows the transducer 3 in cross section. A lens 9 is disposed on the front face of transducer and has a RoC, indicated by surface 8, which is of a value that corresponds to the facing portion of shell 2. The piezoelectric member 10 of transducer 3 is also shown in cross section and has a concave shape of a curvature required to obtain the desired focal length. The matching layer member 12 and backing member 13 of transducer 3 are accordingly provided a curvature corresponding to that of the piezoelectric member 10. Backing member 13 can be advantageously molded on the rear face of the piezoelectric while matching layer member 12 is advantageously machined to the final thickness thereof prior to laminating the matching layer member 12 onto the surface of the piezoelectric member 10.

In FIG. 12, the illustrated cross section of the transducer 3 corresponds to a portion thereof located around a quarter of the transducer length from the edges. At this location, the lens 9 exhibits a RoC 8 smaller than that of FIG. 11, and, to accommodate this, the piezoelectric member 10, matching layer member 12 and backing member 13 are all of a flat shape.

FIG. 13 shows a transducer cross section corresponding to a portion of transducer 3 in the vicinity of the edges thereof where the lens 9 has the smallest value RoC 8. In this region, the curvature of lens 9 is so extreme that piezoelectric member 10 must be made to have convex shape so as to compensate for the short focus of the lens 9. Matching layer member 12 and backing member 13 are shaped accordingly, i.e., are of a corresponding convex shape, as described above in connection with FIGS. 11 and 12.

Figure 14:
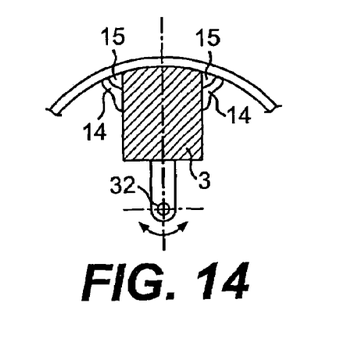
FIG. 14 is a schematic cross sectional view of a further embodiment of the invention showing an arrangement for acoustically coupling the array transducer surface of the probe shell.

Referring to FIG. 14, there is shown a construction that provides good acoustic coupling between transducer 3 and shell 2, and enables smooth movement of transducer 3 relative to shell 2. In this embodiment, the transducer 3 is provided with lip seals 14 attached laterally to the transducer 3 as shown in FIG. 14. The lip seals 14 are advantageously made of a silicon rubber or a rubber elastomer so as to resist wear during use. Further, a quantity of grease or coupling fluid is used to fill the resultant hollow spaces or reservoirs 15 created by lip seals 14, once the transducer 3 is assembled onto the probe. The grease reservoir 15 supplies the necessary quantity of coupling grease to ensure smooth operation of the probe 1. Greases such as graphite filled silicon grease are suitable for this application, although many other greases or high viscosity liquids can be good candidates as well.

It will be understood that a transducer 3 according to a preferred embodiment of the invention is depicted for three different portions thereof in FIGS. 11, 12 and 13 and while these portions are representative of the internal construction of transducer 3, the variation of the RoC, in elevation, for the lens 9 and piezoelectric member 10 is, of course, progressive and must be determined with respect to variation of the lens curvature necessary to achieve conforming shapes for the lens 9 and shell 2.

It is desirable that the piezoelectric member 10, as described above and illustrated in FIGS. 11, 12 and 13, be made up of 1–3 composite material formed by a combination of ceramic pillars and polymer embedding so as to provide increased flexibility and resistance to cracks. Conventional materials such as monolithic ceramics and single crystals are, however, usable so long as the machining process is carefully controlled.

A manufacturing process for making a transducer using a composite material as just described and in accordance with the foregoing descriptions of FIGS. 11, 12, 13 and 14, will now be described. First, a piezoelectric composite member is ground to a predetermined thickness. Electrodes are then deposited on the main faces of the composite member so as to form an array of electrodes. A matching member of quarter wavelength thickness and a flexible interconnection circuit are then laminated onto, respectively, the front and rear faces of the composite member. The laminating set is heated to 60–80° C. for a suitable period and shaping is performed by pressing the set onto the surface of a tool or mold which has the desired final curvature and profile. The shaped piezoelectric set is then maintained in place while the temperature thereof drops back to ambient and the backing material is poured onto the back face of the piezoelectric member so as to maintain the shape so obtained. The transducer is then provided with the silicon lens, corresponding to lens 9, which is molded thereto so as to complete the manufacturing operations.

In a case where monolithic materials are used, mechanical machining of the piezoelectric substrate is used as mentioned above. The 3D shape of the piezoelectric member to be achieved is extremely fragile and requires a series of tools for carrying and handling the material, as well as for electrode plating operations. Further, the matching layer member should be molded, instead of using a bonding process as described above.

Figure 15:
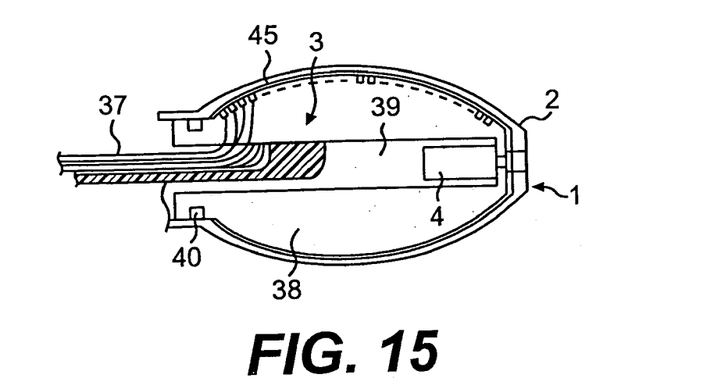
FIG. 15 is a longitudinal cross sectional view of an ovoid embodiment of the hybrid probe of the invention.

Referring to FIG. 15, a further embodiment of the invention is shown. In this embodiment, the principle of providing variable curvature transducers as described above is retained but here the probe shell 2 is designed to be of an ovoid shape with an axis of symmetry located at the center of the probe 1. At least one array transducer 3 is provided which is mounted in contact with the internal surface of shell 2. Transducer 3 is incorporated into a carrier 38 which is in the shape of an ovoid and preferably perfectly fits with the shell surface defining the internal space within shell 2. Carrier 38 includes a hollow space 39 in which are housed the interconnection means 37 of the transducer 3 and a motorization means (e.g., an electric motor) 4 which is preferably located at the distal extremity of hollow space 39.

The coupling function for this embodiment is provided by a film of grease 45 which is applied when the transducer 3 is mounted.

A probe assembled as just described is, therefore, essentially maintenance free. Further, because the interconnection circuits or means 37 are grouped in the central hollow space 39 of the carrier 38, the transducer 3 is capable of undergoing higher rotational amplitudes without damage to the circuits than would otherwise be possible.

For simplicity in the mounting or assembly thereof, shell 2 is preferably constructed as two half shells which are assembled together at a junction 46 (see FIG. 16) to form the desired ovoid probe. It is also desirable to avoid scanning or imaging through the junction 46 of the shell halves, so that it is preferable to swing/tilt the transducer 3 at an angle smaller than or equal to 180 degrees. In this regard, it is noted that a scanning sector angle up to 90 degrees is satisfactory for more than 95% of medical applications being considered here.

Figure 16:
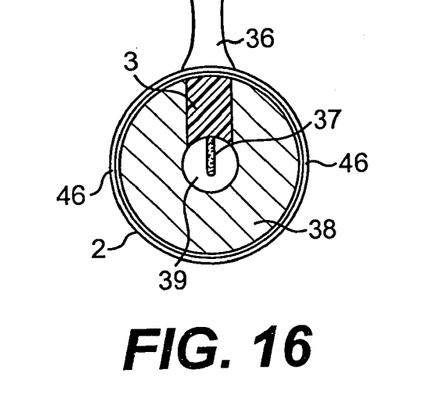
FIG. 16 is a transverse cross sectional view of the ovoid embodiment of the hybrid probe of the invention shown in FIG. 15.

The advantages of the ovoid shell probe are even better appreciated from a consideration of FIG. 16 wherein a central transverse cross section of the ovoid shell 2 is shown. Transducer 3, mounted in carrier 38, is also shown in transverse cross section, and as illustrated, the acoustic beam 36 produced thereby is formed through the shell 2 so as to be directed to the region of interest. In this case, the acoustic window can extend over up to 180 degrees, between the two junctions 26. The hollow space 39 is located centrally and receives the interconnection means 37 as described above. When so assembled, transducer 3 can be swung smoothly around its central position.

Figure 17:
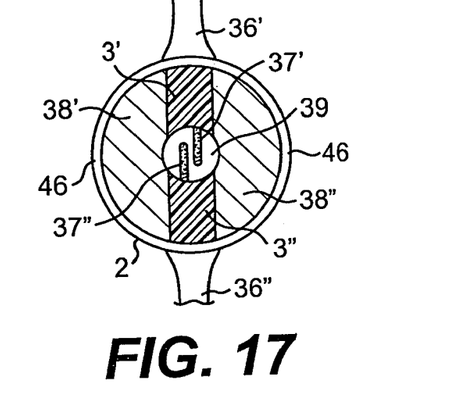
FIG. 17 is a cross sectional view of a further ovoid embodiment of the hybrid probe of the invention.

Referring to FIG. 17, yet another embodiment of the ovoid probe is shown. In this embodiment, a first transducer 3' is mounted in a first carrier portion 38' and produces an acoustic beam 36' and a second transducer 3" is mounted in a second carrier portion 38" and produces an acoustic beam 36". Interconnection means 37' and 37" are respectively associated with transducers 3' and 3". The two transducers 3' and 3" are disposed back to back and are preferably disposed with 180 degree shift with respect to each other. However, other separation angles between the two transducers can also be used. Further, transducers 3' and 3" can be addressed separately to provide alternative images/functions or addressed together in a manner which accelerates the frame rate of images and thus reduces the rendering time for 3D image construction.

According to yet another aspect of the ovoid type probe illustrated in FIG. 17, transducer 3' is devoted to imaging operations while the transducer 3" is designed to emit high intensity ultrasonic energy for treatment operations. In this implementation, the two transducer 3' and 3" need not be identically defined, i.e., the frequency and pitch of the transducers can be determined individually.

Although the invention has been described above in relation to preferred embodiments thereof, it will be understood by those skilled in the art that variations and modifications can be effected in these preferred embodiments without departing from the scope and spirit of the invention.

What is claimed:

1. An ultrasonic apparatus for producing three dimensional images using at least one moving curved array transducer for scanning a volume of a region of interest to be imaged, said apparatus comprising:
   an acoustic front shell having complex shape;
   an ultrasonic transducer adapted for swinging movement underneath said front shell and having a front surface of a shape conforming to the complex shape of said front shell; and
   drive means for providing said swinging movement of the ultrasonic array transducer underneath said front shell so as to scan a volume of the region of interest.

2. An ultrasonic apparatus according to claim 1 wherein the apparatus comprises a mechanical probe, wherein said transducer has a rotation axle, and wherein said drive means comprises a motor mounted in direct driving relation with the transducer through the rotation axle of the transducer.

3. An ultrasonic apparatus according to claim 1 wherein the apparatus comprises a mechanical probe, wherein the array transducer is of a curved linear shape wherein the front shell has an internal surface, and wherein all of the front surface of the transducer conforms to the complex shape of the internal surface of the front shell.

4. An ultrasonic curved array transducer for use in a three dimensional mechanical imaging probe, including a front shell, having an internal surface, disposed in front of the transducer, said transducer comprising:
   an external focusing lens made of silicon rubber and including a front face having variable radius of curvature exactly corresponding to that of the front shell in front of said transducer, said variable radius of curvature varying in a manner such as to minimize the distance separating the front face of the focusing lens and the internal surface of the shell, and
   a piezoelectric member for emitting and receiving ultrasonic energy, said piezoelectric member being assembled beneath said focusing lens and having a variable surface curvature compensating for the variable radius of curvature of the focusing lens in a manner such as to enable the transducer to maintain a common elevational focus for all transducer elements of the array transducer, said transducer having an external elevation surface profile parallel to the corresponding internal profile of the front shell of the probe.

5. An ultrasonic array transducer according to claim 4 wherein the piezoelectric member has a radius of curvature which varies from a concave shape at a center region of the array transducer to a flat shape at outer regions of the array transducer.

6. An ultrasonic array transducer according to claim 4 wherein the piezoelectric member has a radius of curvature which varies from a concave shape at a center region of the array transducer to a convex shape at outer regions of the array transducer.

7. An ultrasonic array transducer according to claim 4 wherein the piezoelectric member has a radius of curvature which varies from a flat shape at a center region of the array transducer to a convex shape at outer regions of the array transducer.

8. An ultrasonic array transducer according to claim 4 wherein the piezoelectric member has a radius of curvature which varies from a concave shape at a center region of the array transducer to a flat shape at an intermediate region of the array transducer and to a convex shape at outer regions of the array transducer.

9. An ultrasonic array transducer according to claim 4 wherein the piezoelectric member is made from a composite ceramic/polymer structure.

10. An ultrasonic mechanical probe comprising a probe housing having an internal surface and a moving array transducer movable relative to said probe housing and including an external surface disposed adjacent to the internal surface of the probe housing, said moving array transducer comprising at least one lip disposed at an edge portion of the moving array transducer located adjacent to said external surface so as to create a reservoir adjacent to the internal surface of the probe housing for retaining a quantity of a coupling fluid such that the coupling fluid moves with the transducer and is coupled to the internal surface of the probe housing.

11. An ultrasonic mechanical probe according to claim 10 wherein said at least one lip comprises a plurality of lips made of silicon rubber.

12. An ultrasonic mechanical probe according to claim 10 wherein said at least one lip comprises a plurality of lips made of elastomeric rubber.

13. An ultrasonic apparatus for producing three dimensional images using a swinging or tilting ultrasonic array transducer, said apparatus further comprising:
- a probe housing having an ovoid portion in which the array transducer is mounted and having an internal surface and a central axis;
- an ovoid shaped carrier of a shape conforming to the internal surface of the said probe housing, said array transducer comprising at least one curved array transducer having a longitudinal axis and being mounted at an angular position within said carrier so as to directly couple acoustic energy to the probe housing and hence to an external media; and
- motorization means disposed at the central axis of the ovoid carrier for tilting or swinging the transducer around said longitudinal axis.

14. An ultrasonic apparatus according to claim 13 wherein the curved array transducer of the ovoid carrier has an external surface conforming to the corresponding internal surface of the probe housing.

15. An ultrasonic apparatus according to claim 13 wherein said ovoid carrier is shaped such that any space between the external surface of said ovoid carrier and the internal surface of the probe housing is reduced to a minimum and wherein said space is filled by a thin film of coupling liquid or grease.

16. An ultrasonic apparatus according to claim 13 wherein said motorization means comprises rotational motorization means located at a center portion of the ovoid carrier so as to provide rotation of the ovoid carrier around a central axis.

17. An ultrasonic apparatus according to claim 13 wherein the said ovoid carrier includes a central hollow space in which is located interconnection means for transducer elements of said array transducer.

18. An ultrasonic apparatus according to claim 13 wherein said ovoid carrier comprises at least a first curved array transducer mounted at a first angular position and a second curved array transducer mounted at a second angular position so as to enable the probe to simultaneously scan two distinct informational volumes.

19. An ultrasonic apparatus according to claim 13 wherein said ovoid carrier comprises at least one first curved array transducer mounted at a first angular position and dedicated to imaging applications and a second curved array transducer mounted at a second angular position and dedicated to high intensity operations in therapy applications.

20. An ultrasonic apparatus according to claim 19 wherein the imaging operation for a given region of interest can be replaced by a high intensity operation using said second transducer operating in the given region.

21. An ultrasonic apparatus according to claim 13 wherein the ovoid carrier is capable of rotating through an angle of more than 360 degrees without damage to interconnection means for said array transducer.

22. An ultrasonic apparatus according to claim 13 wherein the ovoid carrier is provided with at least two oppositely curved array transducers and where the ovoid carrier is capable of rotating through an angle up to 180 degrees.

* * * * *